United States Patent [19]

Austin, Jr. et al.

[11] Patent Number: 5,788,217
[45] Date of Patent: Aug. 4, 1998

[54] CUSPIDOR WATER SUPPLY VALVING

[75] Inventors: George K. Austin, Jr.; Shawn R. Irwin, both of Newberg; Brian E. Bonn, Portland, all of Oreg.

[73] Assignee: A-Dec, Inc., Newberg, Oreg.

[21] Appl. No.: 499,426

[22] Filed: Jul. 7, 1995

[51] Int. Cl.⁶ ................................................. F16K 31/00
[52] U.S. Cl. ........................................ 251/331; 251/331; 4/263
[58] Field of Search ............................. 251/289, 238, 251/293, 239, 295, 331, 213, 231, 236, 242, 243, 244, 245, 246, 240; 4/262, 263, 264, 265, 266

[56] References Cited

U.S. PATENT DOCUMENTS

| | | | |
|---|---|---|---|
| 970,213 | 9/1910 | Goebel | 251/289 |
| 1,036,244 | 8/1912 | Hooper | 251/289 |
| 1,554,013 | 9/1925 | McGovern | 251/289 |
| 1,628,819 | 5/1927 | Brown | 251/289 |
| 1,660,121 | 2/1928 | Fetter | 4/263 |
| 2,039,933 | 6/1936 | Rupert | 251/293 |
| 2,169,324 | 8/1939 | Monnot | 4/263 |
| 2,309,388 | 1/1943 | Gibbons et al. | |
| 2,715,010 | 8/1955 | Reeves | 251/289 |
| 3,019,811 | 2/1962 | Young | 251/243 |
| 3,259,430 | 7/1966 | Beach | 4/263 |
| 3,359,575 | 12/1967 | Nielsen | |
| 3,383,087 | 5/1968 | Linssen | 251/289 |
| 3,400,412 | 9/1968 | Turner | |
| 3,613,131 | 10/1971 | Stram | 4/263 |
| 4,070,000 | 1/1978 | Prescott | |
| 4,280,680 | 7/1981 | Payne | 251/331 |
| 4,307,475 | 12/1981 | Schmidt | |
| 4,836,236 | 6/1989 | Ladisch | 251/331 |
| 4,938,509 | 7/1990 | LaPlante | |
| 4,968,003 | 11/1990 | Danko | 251/331 |
| 5,496,011 | 3/1996 | Samargo | 251/246 |

*Primary Examiner*—John Rivell
*Assistant Examiner*—Ramyar Farid
*Attorney, Agent, or Firm*—Klarquist Sparkman Campbell Leigh & Whinston, LLP

[57] ABSTRACT

The flow of water to a cuspidor bowl-rinse spout and cup-filling spout is controlled by a normally closed valve that is actuated by a lever, the ends of which lever protrude through opposite sides of the cuspidor housing. Either end of the lever may be moved in either of two opposite directions for actuating the valve.

17 Claims, 4 Drawing Sheets

CUSPIDOR WATER SUPPLY VALVING

TECHNICAL FIELD

This invention relates to cuspidor water supply valving for supplying water to rinse the cuspidor bowl or fill a drinking cup.

BACKGROUND INFORMATION AND SUMMARY OF THE INVENTION

A cuspidor is a common component of dental equipment that is normally located immediately adjacent to the dental chair. The cuspidor generally includes a housing that defines a bowl, and a platform upon which may rest a drinking cup. During a dental procedure, a dental patient may be provided with a cup of water for rinsing his mouth. The patient then spits into the cuspidor bowl.

Rinse water is directed into the cuspidor bowl for removing waste through the drain of the cuspidor bowl. The drinking cup is filled from a spout that is normally mounted on the cuspidor near the bowl.

In the past, push-button type controls, one button for controlling cup fill and one for controlling bowl rinse, have been incorporated into cuspidors for controlling the flow of water into the drinking cup and into the bowl of the cuspidor.

This invention is directed to cuspidor water supply valving that provides an elegantly simple lever-actuated valve. The parts that are manipulated by a user to control the valve are located on two opposite sides of the cuspidor housing. Locating these parts on the sides of the cuspidor housing is advantageous because they may be easily reached by both a seated patient and a dental assistant or dentist. Moreover, the valve control mechanisms are readily accessible irrespective of which side of the dental chair the cuspidor is mounted.

Other advantages of the present invention will become apparent to one of ordinary skill in the art upon reading the following detailed description of a preferred embodiment.

DESCRIPTION OF PREFERRED EMBODIMENT

Figure 1:
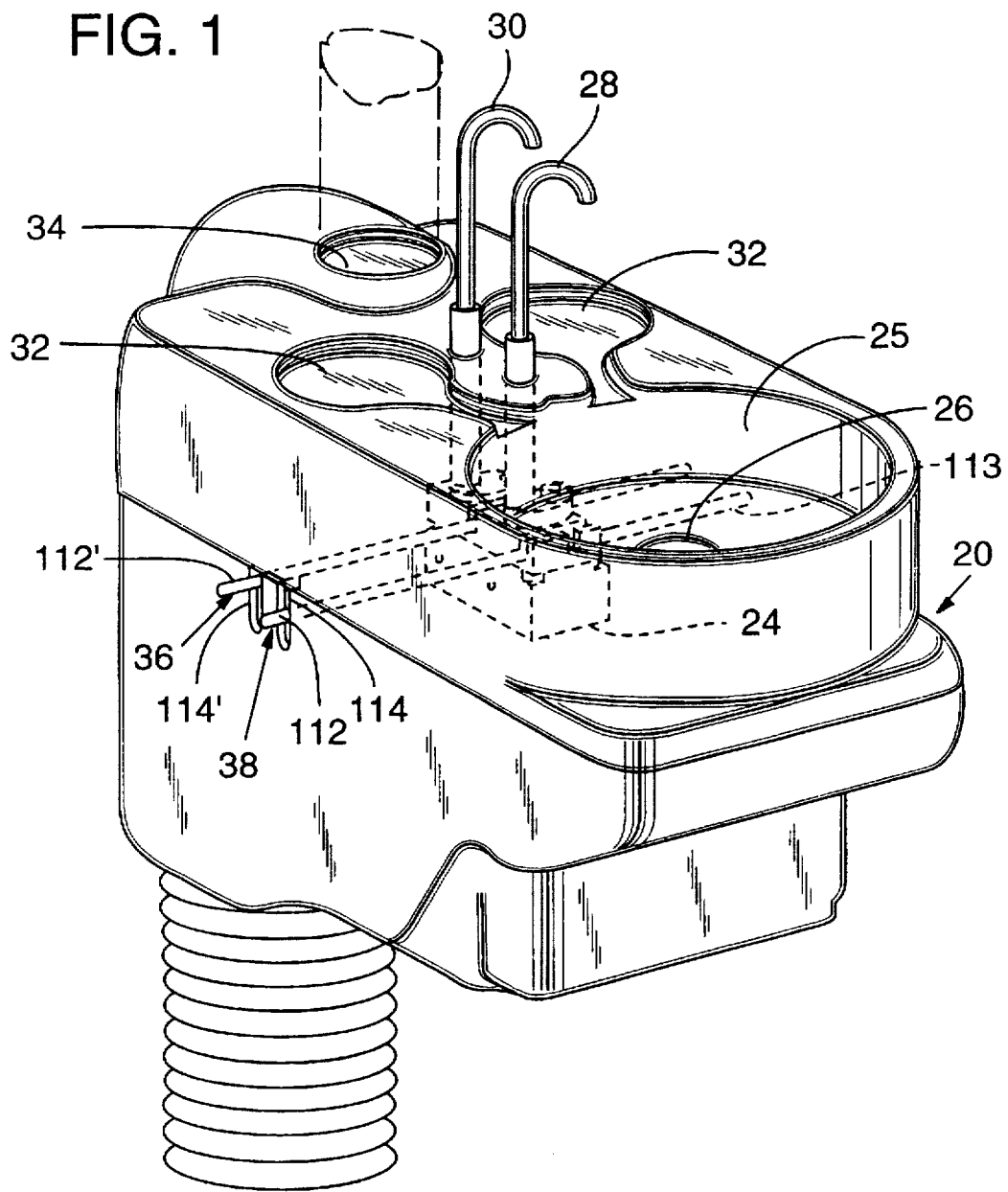
FIG. 1 is a pictorial view of a cuspidor employing the water supply valving of the present invention.

Referring to FIG. 1, there is shown a cuspidor housing 20. The housing encloses a valve assembly 24 in accordance with the present invention. The top of the housing defines a bowl 25 that empties to a drain 26. A bowl spout 28 is activated as described below for rinsing the contents of the bowl 25 into the drain 26.

A cup-fill spout 30 is located near the bowl spout 28 and is operable for filling a drinking cup that may be placed in either of two recesses 32 formed in the top of the cuspidor housing. The cuspidor housing may include another opening 34 through which a support post projects. The cuspidor and/or an overhead light may be mounted to the post.

The valve mechanism 24 is operated by a pair of levers 36, 38, for respectively directing water to the bowl spout 28 and the cup-fill spout 30. The ends of the levers protrude from opposing sides of the cuspidor housing. As will be explained, either end of each lever may be moved in either of two directions to direct water to an associated spout.

Figure 2:
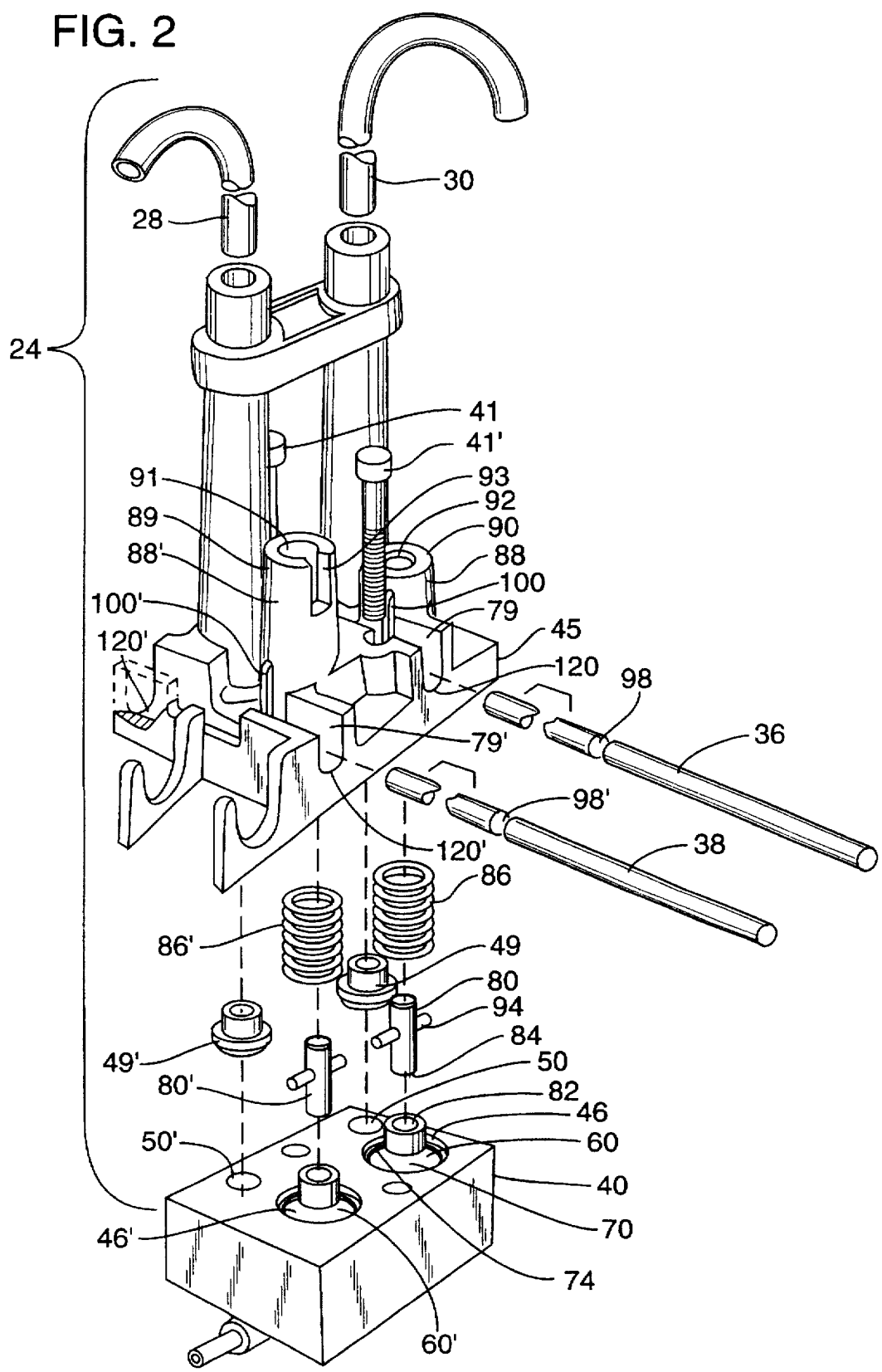
FIG. 2 is an exploded pictorial view of the primary components of the valving.
Figure 3:
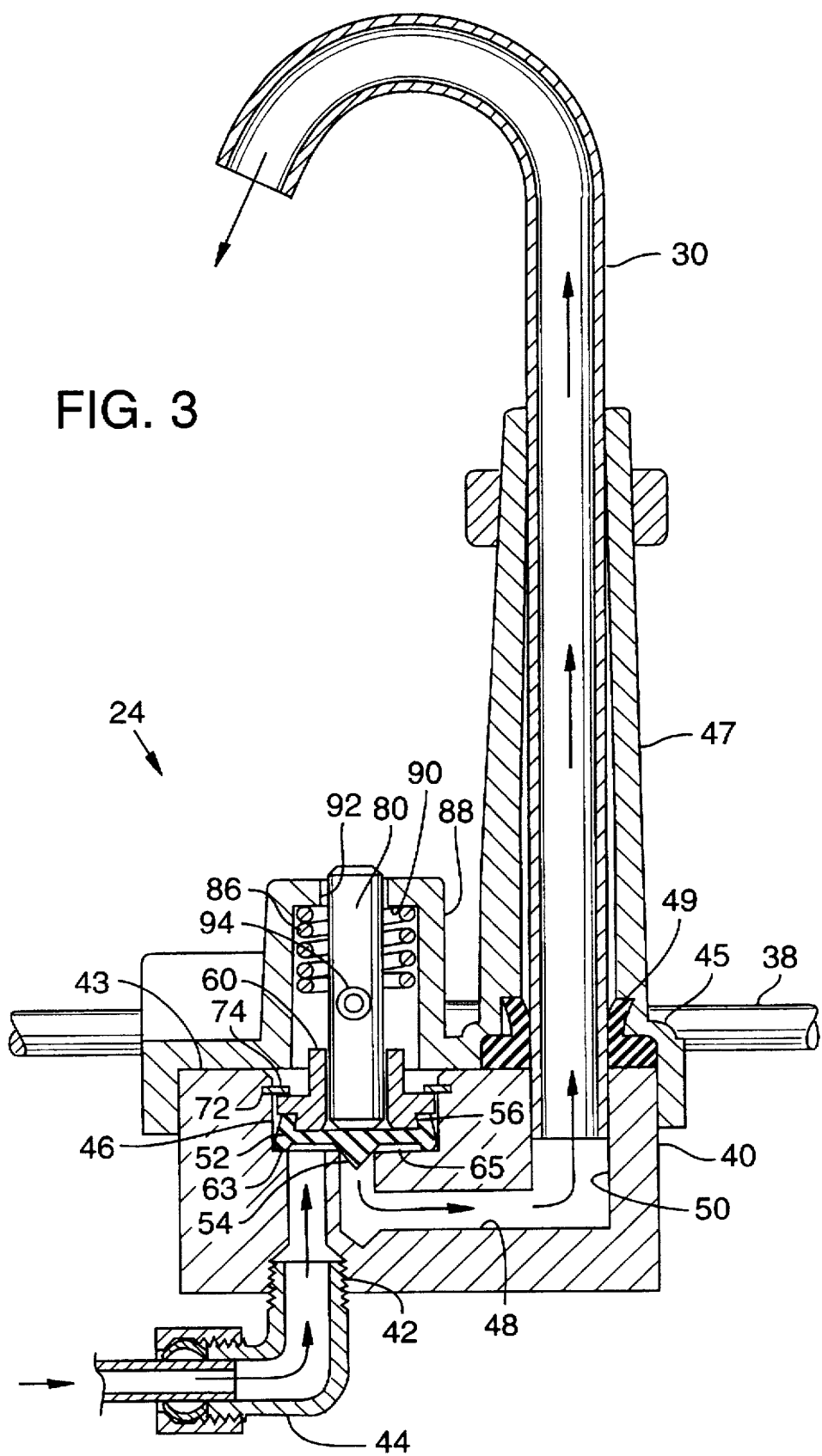
FIG. 3 is a front cross-sectional view of the valving showing a water flow path therethrough.
Figure 4:
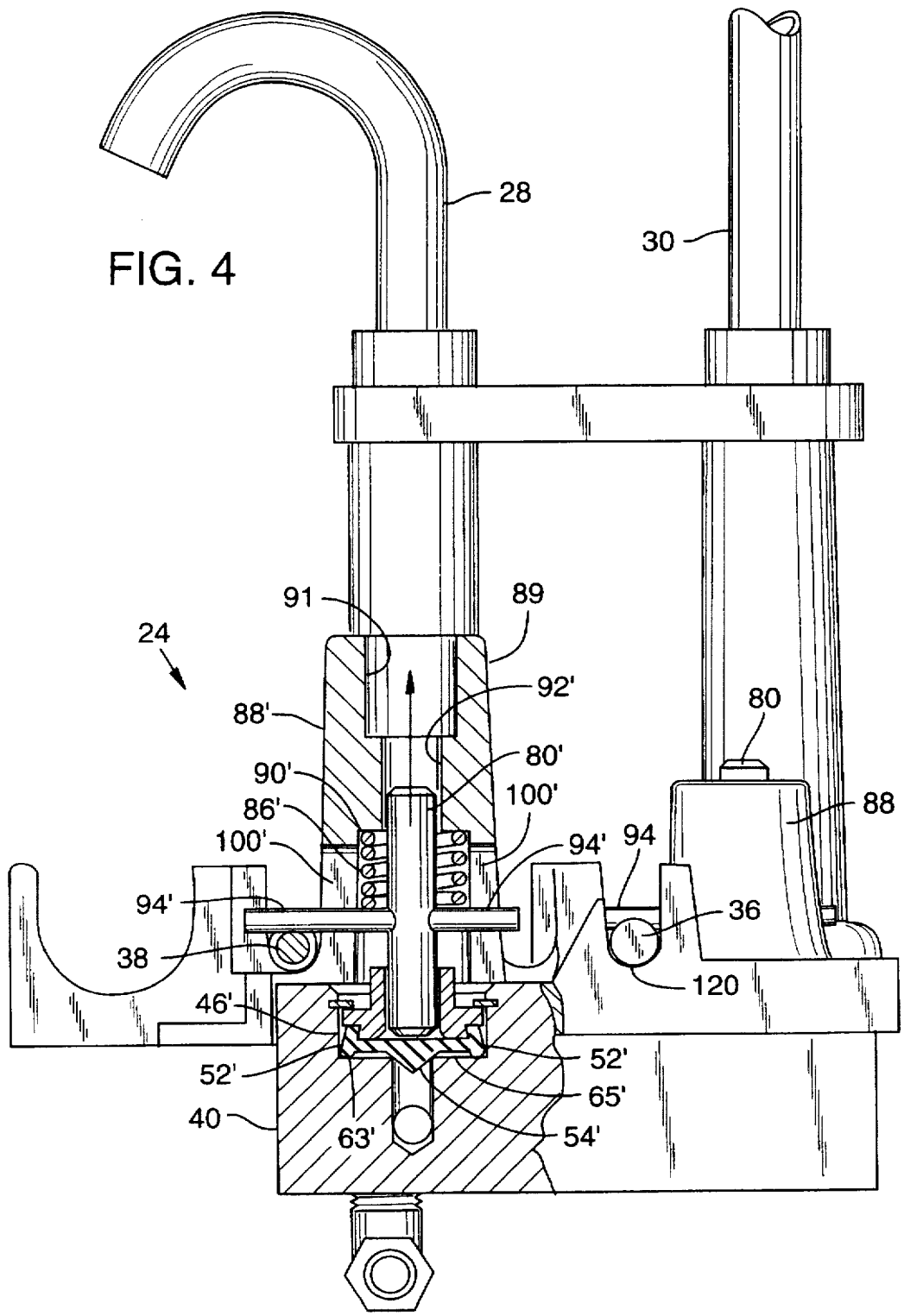
FIG. 4 is a side view of the valving, partly broken away to depict actuation mechanisms.

Turning to the particulars of the water supply valving of the present invention and with reference to FIGS. 2-4, a preferred embodiment of the invention includes the valve assembly 24, which comprises a manifold block 40 having formed into its underside an inlet conduit 42 (FIG. 3). A water supply conduit 44 is connected to the inlet 42. The inlet 42 opens into the bottom of a generally cylindrical valve cavity 46 formed in the block 40.

One end of an outlet conduit 48 (FIG. 3) opens to the center of the bottom of the valve cavity 46 so that a passage for water flow from the inlet, through the cavity, and into the outlet 48 is defined. The other end of the outlet 48 is contiguous with a spout aperture 50 that is formed in the top surface 43 of the block 40. One end of the cup-fill spout 30 is fit within the spout aperture 50 and sealed to the manifold, as described next.

A manifold top 45 is fastened, via screws 41, to the top surface 43 of the manifold block 40. The manifold top 45 defines an upwardly protruding tube 47 into which is inserted the lower end of the spout 30. The central opening of the tube 47 is aligned with the spout aperture 50. At the junction of the manifold top 45 and the manifold surface 43, the interior of the tube 47 is shaped to receive a flanged-end, resilient cylindrical seal 49 that is firmly compressed to surround the spout 30 and seal the connection of the spout 30 to the manifold block 40.

It is noteworthy here that although the present portion of this description relates to the parts of the valve assembly 24 that are operable for providing water to cup-fill spout 30, the manifold 40 and manifold top 45 are also configured to have another water inlet, spout tube, seal, and associated valve mechanisms for providing water to the bowl spout 28 of the valve assembly. For the sake of brevity, however, this portion of the description is generally limited to the mechanisms for supplying water to the cup-fill spout 30, with the understanding that substantially identical mechanisms (indicated in the drawings with a common reference numeral and prime symbol) are incorporated for supplying water to the bowl spout 28.

An elastomeric diaphragm 52, is located in the bottom of valve cavity 46 and movable to plug the outlet 48 at the cavity, hence occluding flow to the outlet. The diaphragm 52 is mounted on one end of a rigid guide member 60 that fits in the cavity 46. Specifically, the diaphragm 52 is a generally cup-shaped member that opens upward (FIGS. 3 and 4) and has a downwardly protruding, conical-shaped plug 54 that fits snugly within the opening of the outlet 48. The upwardly protruding side wall 56 of the diaphragm fits tightly over a generally frustum-shaped lower end of the guide member 60 that carries the diaphragm. That end of the guide member is shaped so that the side wall 56 of the diaphragm is firmly compressed against the side wall of the valve cavity 46.

An annular rim 63 of the diaphragm protrudes downwardly from the side wall 56 thereby to define between the rim, cone and cavity bottom an annular plenum 65. The plenum is in fluid communication with the inlet 42. When the outlet 48 is plugged, the inlet water fills and pressurizes the plenum 65. This pressure acting on the rim 63 urges the rim against the cavity side wall for enhancing the sealing action of the diaphragm 52, supplementing the seal provided by the plug 54.

The guide member 60 has a reduced diameter at its upper end, thereby defining an annular shoulder 70 in the guide member (FIG. 2). That shoulder 70 is generally aligned with an annular groove 72 (FIG. 3) formed in the cavity side wall. A spring-type retainer clip 74 is deformed to fit tightly within the groove 72 and extend across the shoulder 70 of the guide member 60, thereby retaining the guide member and attached diaphragm within the cavity 46.

A rigid, cylindrical, elongated plunger 80 fits through a central bore 82 of the guide member 60 (FIG. 2). One end 84 of the plunger 80 bears on the diaphragm just above the plug 54.

A compressed spring 86 is retained within a generally hollow cylindrical retainer housing 88 that is a part of the manifold top 45. The retainer housing 88 includes an internal top 90 surface against which one end of the spring 86 bears. The housing 88 includes an aperture 92 corresponding to the diameter of the plunger 80 and through which the plunger 80 is guided to move upwardly and downwardly.

The other end of the spring 86 bears against a rigid arm 94 (which may be configured as a roll pin extending through a transverse hole in the plunger 80) that is fastened to extend perpendicularly from the long axis of the plunger 80 on either side thereof. The spring 86, therefore, normally biases the plunger 80 against the diaphragm 52 so that the diaphragm plug 54 occludes the outlet 48.

One end of the arm 94 extends over and fits into a central groove 98 formed in the above-mentioned lever 36 (FIG. 2). When the ends of the lever 36 are moved, as will be described, the arm 94 is lifted to compress the spring 86 and overcome the spring bias on the plunger 80, and the plunger 80 is guided to move along its long axis through the bore 82 of the guide member 60 and through the aperture 92 in the retainer housing 88.

The sides of the spring retainer housing 88 have formed through them diametrically opposed clearance slots 100 (one slot appearing in FIG. 2). The slots 100 are sized to permit the opposite ends of the arm 94 (which ends protrude from the retainer housing 88) to move upwardly and downwardly with the plunger 80.

The upward movement of the plunger 80 permits the diaphragm 52 to deform away from the outlet 48 by an amount sufficient to permit a gap between the plug 54 and the outlet 48 so that water flows through the inlet 42 and outlet 48 into the spout 30.

The levers 36, 38 for opening the valves (that is, lifting plungers 80, 80') are carried in grooves 79, 79' formed in the manifold top 45. In a preferred embodiment, the elongated rigid lever 38 is sized so that one end 112 protrudes through an elongated slot 114 formed in the side of the cuspidor housing (FIG. 1). The opposite end 113 of the lever 36 protrudes through an elongated slot formed in the opposite side of the cuspidor housing. With reference to FIGS. 3 and 4, the levers 36, 38 that are carried on the manifold block are each pivotable to move against an arm 94, 94' of a plunger 80, 80' thereby to overcome the spring bias of the plunger and actuate or open the associated water flow passage to the spout 28, 30. When a lever is released, the spring returns the plunger end against the diaphragm to occlude the outlet.

The arm 94, which seats within the central groove 98 in the lever 36, is located between the outermost edges 120 of the groove 79 in which the lever is carried (both edges 120' of the corresponding groove 79' that carries lever 38 are shown in FIG. 2). These edges 120 provide two separate fulcrums against which the lever 36 is pivotable when either of the opposing exposed ends 112, 113 of the lever is lifted or depressed by the user. For example, when the end 112 of lever 36 is lifted, the groove edge 120 most distant from that end acts as a fulcrum, and the lever lifts the arm 94 and connected plunger 80 to open the valve. When lever end 112 is depressed, the opposite groove edge 120 acts as a fulcrum, and the lever also lifts the arm 94 and plunger 80. It will be appreciated, therefore, that the valving is actuated by moving either one of the opposing ends 112, 113 of the levers 36, 38 in either of two opposing directions.

Inasmuch as the ends of the levers 36, 38 protrude through slots formed in the side of the housing, there is no need to add additional passages to the top of the cuspidor housing 20 for receiving push-button type controls for the cuspidor valving. Since the top surface of the cuspidor housing 20 is most likely to receive spilled liquids, etc., this reduction in the number of top passages through the housing is advantageous for minimizing the opportunity for contaminants to enter the housing. Moreover, the lever-actuated valve assembly provides a reliable, mechanical system that requires practically no maintenance, except for the occasional replacement of the diaphragm.

As best shown in FIGS. 2 and 4, the retainer housing 88' associated with the valve bowl spout 28 includes a generally cylindrical extension 89 into which is counterbored a cavity 91. The extension and cavity provide a location for mounting a push-button type hanger valve, the actuator of which is moved as a result of the upward movement of the stem 80. The hanger valve may be, for example, generally cylindrically shaped to conform to the shape of the cavity 91, with the actuator adjacent the top of the stem 80'. FIG. 2 depicts a slot 93 through which may extend tubing barbs for connecting the hangar valve to pneumatic conduit. A set screw (not shown) is threaded through the wall of the extension to secure the hanger valve to the extension.

It is contemplated that the just-mentioned hanger valve would be employed, upon actuation, for controlling another valve, a bowl rinse timing valve, for directing rinse water flow through the bowl rinse spout 28 for a predetermined period of time. In such an instance, water would not be supplied to valve cavity 46', although, as noted, the mechanisms for actuating that valve (lever 38, plunger 80', etc.) would serve to actuate the hanger valve. It will be appreciated, therefore, that the above-described extension 91 permits a dual use of those mechanisms.

Although the foregoing has been described in connection with preferred and alternative embodiments, it will be appreciated by one of ordinary skill in the art that various modifications may be substituted for the mechanisms and method described here without departing from the invention as defined by the appended claims and their equivalents.

The invention claimed is:

1. A water supply valving apparatus for a cuspidor, comprising:

a housing having sides, and a top that includes a bowl formed therein;

a spout carried by the housing to protrude from the top of the housing;

a normally closed valve assembly enclosed by the housing and having at least first and second sides, and including a valve that is openable for directing water to the spout;

a lever mechanism connected to the valve assembly and including a lever that is arranged to have one end protruding outside of a side of the housing and another end protruding outside another side of the housing, the protruding ends of the lever being movable for opening the valve; and wherein the valve assembly defines a groove having a first end adjacent the first side of the valve assembly and wherein the first end of the groove acts as a first fulcrum against which the lever is pivotable to open the valve; and wherein the valve assembly comprises a manifold assembly having a water inlet and outlet defined therein; a diaphragm; and an actuator mounted to the manifold assembly and biased to push the diaphragm into position to occlude a passage between the inlet and outlet, and wherein the manifold assembly carries the lever and defines the first fulcrum about which the lever pivots to move the actuator against its bias thereby to permit the diaphragm to move away from and open the passage.

2. The apparatus of claim 1 wherein the groove has a second end, the first and second ends of the groove being connected by a straight surface, the surface engaging the lever between the first and second ends.

3. The apparatus of claim 2 wherein the second end acts as a second fulcrum, the lever being pivotable against the second fulcrum to open the valve.

4. The apparatus of claim 1 wherein the diaphragm is elastomeric and includes a rim portion that defines an annular plenum that is in fluid communication with the inlet when the passage is occluded.

5. The apparatus of claim 1 wherein the valve includes:

a plunger that is biased so that one end thereof is pushed against the diaphragm; and an arm fastened to the plunger to extend therefrom across a path of the pivotally moved lever so that the movement of the lever is transferred to the plunger by the arm.

6. The apparatus of claim 5 further comprising a guide member mounted to the manifold assembly to constrain the plunger to translational movement.

7. The apparatus of claim 5 further comprising a spring retained about the plunger for biasing the plunger to push against the diaphragm.

8. A water supply valving apparatus for a cuspidor, comprising:

a housing having sides, and a top that includes a bowl formed therein;

a spout carried by the housing to protrude from the top of the housing;

a normally closed valve assembly enclosed by the housing and including a valve that is openable for directing water to the spout;

a lever mechanism connected to the valve assembly and including a lever that is arranged to have a first end protruding outside of a side of the housing and a second end protruding outside of another side of the housing, the protruding ends of the lever being movable for opening the valve; and wherein the valve assembly defines a groove having a first end and a second end the groove extending between a first fulcrum and a second fulcrum and wherein the first fulcrum is defined by the first end of the groove and is located so that the lever if pivotable against the first fulcrum to open the valve; and the second fulcrum is defined by the second end of the groove and is located so that the lever is pivotable against the second fulcrum to open the valve.

9. The apparatus claim 8 wherein the lever is arranged so that the first protruding end thereof may be moved in either of two opposing directions for opening the valve.

10. The apparatus of claim 8 wherein the lever is arranged so that the protruding second end thereof may be moved in either of two opposing directions for opening the valve assembly.

11. The apparatus of claim 8 further comprising an actuator connected between the lever and the valve assembly and a valve mounting member mounted adjacent to the actuator and defining a cavity into which part of the actuator moves when the lever moves for opening the valve.

12. The apparatus of claim 8 wherein the lever rests in the groove.

13. The apparatus of claim 12 wherein the lever is a cylindrical rod.

14. The apparatus of claim 8 wherein the groove has a surface that extends between the first and second ends, and wherein the lever engages the surface between the two ends.

15. A water supply valving apparatus for a cuspidor, comprising:

a housing having sides and a top that includes a bowl formed therein;

a spout carried by the housing to protrude from the housing;

a normally closed valve assembly enclosed by the housing and including a valve that is openable for directing water to the spout, the valve assembly defining a groove having a first edge adjacent one side of the housing and a second edge adjacent an opposite side of the housing; and a lever mechanism connected to the valve assembly including an elongate lever arranged to have a first end protruding from one side of the housing and positioned near the first edge of the groove and a second end protruding from the opposite side of the housing and positioned near the second edge of the groove, the first protruding end of the lever being pivotable against the second edge of the groove to open the valve, and the second protruding end of the lever being pivotable against first edge of the groove to open the valve.

16. The apparatus of claim 15 wherein the groove has a surface extending between the sides of the housing and the lever fits, at least partially, within the groove.

17. The apparatus of claim 15 wherein the groove is substantially linear between the first and second edges and the lever rests in the groove.

\* \* \* \* \*